United States Patent
Meskanen

(10) Patent No.: US 9,103,765 B2
(45) Date of Patent: Aug. 11, 2015

(54) METHOD AND APPARATUS FOR DETERMINING THE DIMENSIONS AND EXTERNAL PROPERTIES OF THREE-DIMENSIONAL OBJECTS SUCH AS SAWN TIMBER

(71) Applicant: FIN SCAN OY, Espoo (FI)

(72) Inventor: Urpo Meskanen, Espoo (FI)

(73) Assignee: FIN SCAN OY, Espoo (FI)

( * ) Notice: Subject to any disclaimer, the term of this patent is extended or adjusted under 35 U.S.C. 154(b) by 0 days.

(21) Appl. No.: 13/782,974

(22) Filed: Mar. 1, 2013

(65) Prior Publication Data
US 2013/0229670 A1   Sep. 5, 2013

(30) Foreign Application Priority Data

Mar. 2, 2012  (FI) ..................... 20125234

(51) Int. Cl.
  *G01N 21/13*   (2006.01)
  *G01B 11/245*   (2006.01)
  *G01N 21/898*   (2006.01)
  *G01N 33/46*   (2006.01)

(52) U.S. Cl.
  CPC ............. *G01N 21/13* (2013.01); *G01B 11/245* (2013.01); *G01N 21/8986* (2013.01); *G01N 33/46* (2013.01)

(58) Field of Classification Search
  CPC .. G01B 11/245; G01B 11/105; G01B 5/0035; G01N 21/13; G01N 21/8986; G01N 33/46
  USPC ........ 356/625–640, 237.1–237.6; 348/89, 91, 348/86, 88, 92, 94, 95
  See application file for complete search history.

(56) References Cited

U.S. PATENT DOCUMENTS

| 6,031,567 A | 2/2000 | Johnson |
| 6,122,065 A | 9/2000 | Gauthier |

FOREIGN PATENT DOCUMENTS

WO    WO 00/62011 A1    10/2000

*Primary Examiner* — Tri T Ton
(74) *Attorney, Agent, or Firm* — Birch, Stewart, Kolasch & Birch, LLP

(57) ABSTRACT

The present application relates to a method and apparatus for determining the dimensions and external properties of three-dimensional objects such as sawn timber, in which method objects like timber are moved in a transverse position over a target area in conveying direction, the target area is illuminated, and the target area is scanned upwards by a camera. In accordance with the invention each object like timber is scanned or exposed at least twice in the target area, and the timber is conveyed in the target area over support bars, which are in an angle (α) in relation to the conveying direction.

12 Claims, 2 Drawing Sheets

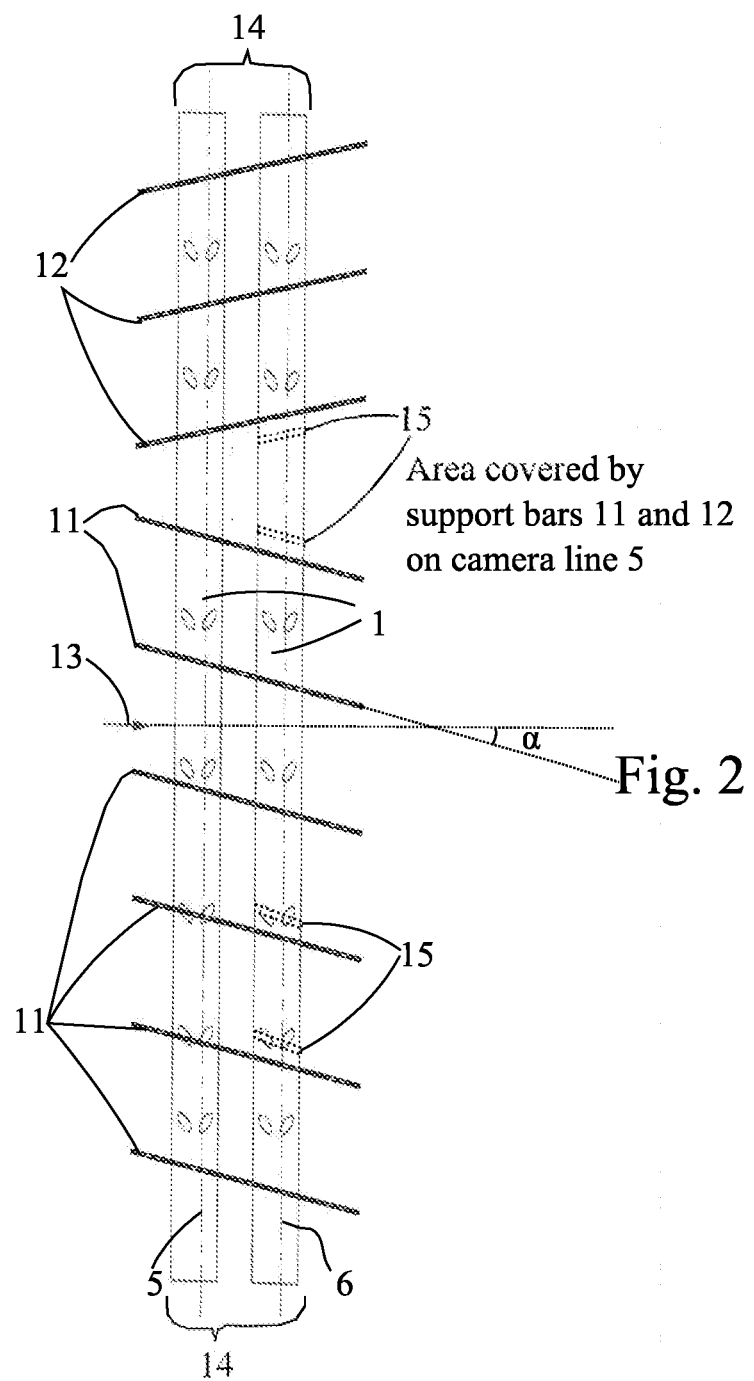

Figure 1:
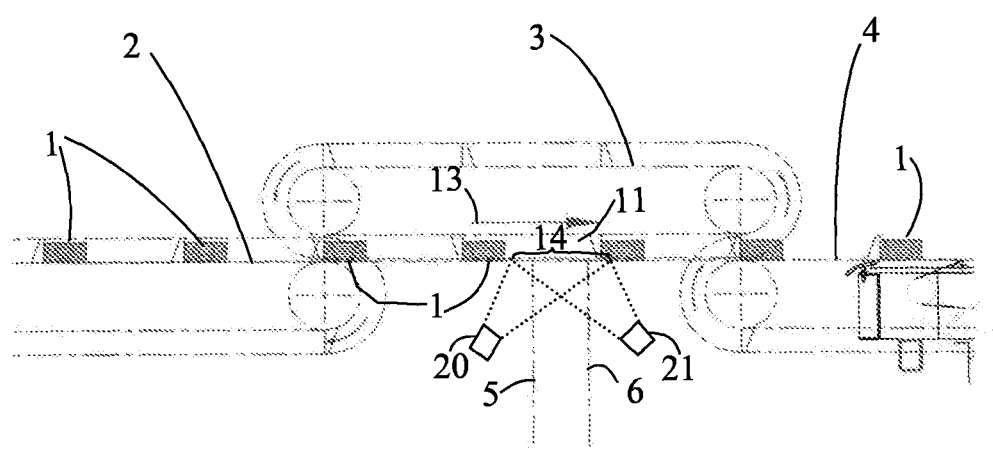

METHOD AND APPARATUS FOR DETERMINING THE DIMENSIONS AND EXTERNAL PROPERTIES OF THREE-DIMENSIONAL OBJECTS SUCH AS SAWN TIMBER

The invention relates to a method according to the preamble of claim 1 for determining the dimensions and external properties of three-dimensional objects such as sawn timber by transverse measurement.

The invention also relates to an apparatus suited for implementing the method.

As to the prior art, FI laid-open publication 56,451 describes a method in which the top surface of sawn timber being measured is illuminated with radiation emitted at two different wavelengths in order to detect the shape of both edges of the sawn timber. The method requires the use of special light sources or, alternatively, color filters that reduce the available light output.

FI laid-open publication 85,915 describes a transverse measurement method in which color information on the object being measured is obtained using only one color camera.

FI patent application 945,743, FI patent 100,486 and EP patent application 595,438 describe embodiments suited for determination of timber dimensions based on the concept of feeding the object to be measured via the measurement equipment in the longitudinal direction. The greatest drawback of longitudinal measurement is the limited capacity (one-third) of that of transverse measurement. Technology developed for longitudinal measurement is not applicable to transverse measurement, because all measurement and illumination equipment used in transverse measurement must be located above the path of travel due to risk of dirt accumulation. In transverse measurement, conveyor structures prevent installation of measurement and illumination equipment underneath the path of travel.

PCT/FI00/00270 describes a solution, where the object under measurement, like timber is scanned by means of color line cameras from three separate directions in a transverse-measuring arrangement in a single measurement station equipped with one simultaneous illumination arrangement. This publication does not describe a solution, where also the bottom face of the timber is scanned with cameras positioned under the timber.

The problem with the prior art solutions is that the camera under the timber does not typically get a full view of the object's, like timber's bottom face because there are supporting structures obstructing the view. The unscanned area is typically around 10% and the problem is therefore remarkable.

The solutions which flip the object upside down for taking a view from both sides is an expensive solution and does not allow high operation speeds. The solutions which use drum type of turner require a larger space and are expensive.

It is an object of the invention to overcome the drawbacks of the prior-art techniques and to provide an entirely novel type of method and apparatus for determination of dimensions and external properties of timber.

The goal of the invention is achieved by scanning the object under measurement by means of cameras positioned below timber in such a way that the timber is supported above the cameras in such a way that the support bars are in an angle in relation to the movement of the timber. In the target area the timber is scanned or exposed at least two consecutive times, either scanned with two line cameras or exposed with a matrix camera two separate times. Advantageously the angle α between the support bars and the movement of the timber is in the range of 10-30° most advantageously around 15°.

In some preferred embodiments the cameras are either line cameras or matrix cameras, both color cameras and monochromatic cameras can be used.

Typically the area for viewing (target area) the timber is horizontal or a slight uphill or downhill, typically in the range of 10-30 degrees.

More specifically, the method according to the invention is characterized by the specifications disclosed in the characterizing part of claim 1.

Furthermore, the apparatus according to the invention is characterized by what is stated in the characterizing part of claim 5.

The invention offers significant benefits.

By virtue of using the skewed support bars and two exposures for the object to be measured like timber, the object will be measured completely also from the bottom side.

Complicate mechanical solutions for flipping or turning the objects may be avoided.

In the following, the invention is described in more detail by way of exemplifying embodiments illustrated in the appended drawings in which FIG. 1 is a side view of one embodiment of the invention;
FIG. 2 is a bottom view the embodiment of FIG. 1.

In the description of the invention, the elements thereof are designated by the following reference numerals:
angle of the support bars 11 and 12 α
timber 1
first lug chain conveyor 2
second lug chain conveyor 3
third lug chain conveyor 4
first line camera 5
second line camera 6
First support bars 11
Second support bars 12
Conveying direction 13
Target area 14
Covered area at first exposure 15
Light units 20
Light units 21

In accordance with FIG. 1 timber 1 is typically optically examined by line cameras 5 and 6 or matrix camera covering the target area. In FIGS. 1 and 2 only the cameras 5 and 6 which are viewing the bottom side of the timber 1 are presented. Typically in these solutions the top face and side faces of the timber are scanned in a separate scanning station either before or after scanning the bottom face. The target area 14 is also illuminated by light units 20 and 21.

The timber to be measured travels in a transverse position on the conveyors 2, 3 and 4, which are typically lug chain conveyors. Typically, the width of the conveyors 2, 3 and 4 is from 2 to 10 m. According to the invention, the bottom side of the object to be measured (timber 1) is scanned in a single measurement station including to line cameras 5 and 6 or alternatively one matrix camera (not presented) positioned below the timber 1. The target area 14 around cameras 5 and 6 is typically illuminated by light units 20 and 21. The illuminated area is scanned by the first line camera 5 and by the second line camera 6. By matrix camera, a larger area has to be illuminated and the light distribution has to be at least essentially uniform.

The purpose of scanning the timber 1 by cameras 5 and 6 is to automatically determine quality and optimize cuttings. By scanning the dimensions and external properties of timber are determined like length thickness and width and also properties for defects like wane edges, rot, knots, resin and colour defects affecting the value of the timber.

The timber is conveyed forward by traverse lug chain conveyers 2, 3 and 4 transporting the timber 1 with help by chains and lugs attached to them. Today, speed for scanning is typically 100-250 pieces of timber/minute.

A traditional way to scan the timber 1 is to use two scanning stations and flip timber mechanically between these two stations. Mechanical flipping is difficult and causes disturbances with high speeds. The flipping device requires also a lot of space and is expensive. The of use drum type of turner requires a larger space and is expensive.

In accordance with the invention the timber is scanned at two scanning sites 5 and 6 over which the timber 1 is conveyed. The bottom support structures of one lug chain conveyer 3 are removed and replaced by thin support bars 11 and 12, which are slightly in an angle α relative to a conveying path and in a conveying direction 13, typically in an angle α of 5-30 degrees relative to the conveying direction 13. The support bars 11, 12 are fixed immediately below the conveying path on any suitable support. The support bars support the timber 1 as the lugs of the upper conveyor 3 convey the timber along the conveying path in the conveying direction 13. Like presented in FIG. 2, the support bars 11 and 12 may be skewed in different directions in order to avoid traverse movement of the timber 1.

The area of cameras 5 and 6 and bars 11 and 12 forms a target area 14.

In FIG. 2 by reference number 15 is indicated the areas covered by support bars 11 and 12 on camera line 5, yet visible later for on camera line 6 due to the skewed support bars 11 and 12.

First 2 and third 4 conveyers are conveying the timber 1 on their upper side and these conveyers are interlaced with the second conveyer 3, which is conveying the timber on its bottom part.

The first scanning is made through the skewed support bars 11 and 12 by first camera 5 and the second scanning a short time later by second camera 6, when timber has moved a length corresponding the distance of cameras 5 and 6 from each other. Then the parts 15 of timber 1 hidden behind the bars 11 and 12 are now visible for the second camera 6 due to the skewness of the bars 11 and 12.

The scanning can be done like in FIGS. 1 and 2 by two line cameras or row of line cameras, or alternatively by a matrix camera or a row of matrix cameras covering the target area 14 presented in FIG. 2, by making two consecutive exposure such that a first exposure is made while the timber 1 is in the target area 14 at camera line 5 and second exposure while the timber is moved at least the distance corresponding the distance between camera lines 5 and 6.

The length and angle α of the support bars 11 and 12 are defined such that the timber in the different scanning positions 5 and 6 can be completely scanned. In other words all parts 15 of timber hidden by scanning by first camera 5 should be revealed on the second scanning by the second camera 6. Also, the mechanical structure of bars 11 and 12 may not disturb essentially the conveying of the timber 1.

In practice the second conveyor 3 of the measurement arrangement may be arranged either horizontally or slated downhill or uphill.

What is claimed is:

1. Method for determining the dimensions and external properties of three-dimensional objects such as sawn timber, in which method
   conveying the objects over a target area along a conveying path,
   illuminating target area along the conveying path, and
   scanning the target area with a camera facing generally upwardly so that each object is scanned or exposed at least twice in the target area, and
   providing support bars, within the target area, fixedly arranged immediately below the conveying path, the support bars supporting the objects within the target area and being arranged at an angle (α) in relation to the conveying path, wherein angle (α) between the support bars and the conveying path is between 5-30, preferably around 15 degrees.

2. Method according to claim 1, wherein the scanning is performed by two line cameras.

3. Method according to claim 1, wherein the scanning is performed by matrix cameras with two exposures.

4. Method according to claim 1, wherein the timber is conveyed by chain or belt conveyors.

5. Apparatus for determining the dimensions and external properties of three-dimensional objects such as sawn timber, comprising
   a conveyor system moving objects over a target area along a conveying path,
   for a radiation source illuminating the target area,
   a camera upwardly scanning the target area the,
   for a scanner scanning each object at least twice in the target area, and
   support bars fixedly arranged immediately below the conveying path in the target area, which are in an angle (α) in relation to the conveying direction, the support bars supporting the objects while conveyed over the target area, wherein angle (α) between the support bars and the conveying direction is between 5-30, preferably around 15 degrees.

6. An apparatus according to claim 5, wherein the scanning means are two line cameras.

7. An apparatus according to claim 5, wherein the scanning means is a matrix camera performing two exposures.

8. An apparatus according to claim 1, wherein the conveyor system conveys said timber using chain or belt conveyors.

9. The method of claim 4 wherein said conveying of the objects within the target area supplies a conveying force to said objects from a direction other than below.

10. The method of claim 4 wherein the objects are conveyed along the conveying path by lugs extending downwardly into said conveying path in the target area, the lugs being driven by an endless conveyor located above the conveying path in the target area and slidably translating the objects across said support bars.

11. The apparatus of claim 8 wherein said conveyors include lugs and wherein the conveyor of said conveyor system supplying a conveying force to said objects within the target area is a chain or belt conveyor provided above said target area.

12. The apparatus of claim 11 wherein said conveyor supplying a conveying force to said objects within the target area supplies this conveying force from downwardly extending lugs slidably translating said objects across said support bars.

* * * * *